United States Patent [19]

Bradford

[11] Patent Number: Plant 5,653

[45] Date of Patent: Feb. 4, 1986

[54] DWARF NECTARINE TREE (RED FANTASTIC)

[76] Inventor: Norman G. Bradford, 11875 E. Savana Rd., Le Grand, Calif. 95333

[21] Appl. No.: 622,082

[22] Filed: Jun. 18, 1984

[51] Int. Cl.[4] ..... A01H 5/03

[52] U.S. Cl. ..... Plt./41

[58] Field of Search ..... Plt./41

*Primary Examiner*—Robert E. Bagwill

*Attorney, Agent, or Firm*—Vergil L. Gerard

[57] ABSTRACT

The instant variety of nectarine tree is a new and distinct genetic dwarf variety broadly characterized by a vigorous, drooping tree which reaches six feet in height and bears clingstone fruit possessing many of the characteristics of color, size, firmness and flavor generally found in nectarine fruit produced by full size trees. The fruit ripens during the first week of August under the ecological conditions described, in the San Joaquin Valley of California, and is of large size when compared to fruit of other genetic dwarf nectarine trees. The fruit is of excellent eating and shipping quality, has extreme crispness and firmness, and has an attractive red blush and waxy skin.

1 Drawing Figure

BACKGROUND OF THE VARIETY

The fruit of the instant variety of genetic dwarf nectarine tree most nearly resembles Sunbonnet (U.S. Plant. Pat. No. 3,325), a genetic dwarf nectarine, but is distinguished therefrom by its fruit being of larger size, having a redder skin color, and excellent crispness and firmness. The fruit ripens for first picking about five days after Sunbonnet. The instant variety is an improvement on the Sunbonnet variety and other varieties of genetic dwarf nectarines known to me by its large size fruit which is substantially equal in size to the fruit of full size nectarine trees, and by its extreme firmness and crispness, attractive red skin color, and waxy appearance.

The instant variety was developed by me at Bradford Farms in Merced County, Calif., as the second generation resulting from the pollination of an unnamed dwarf seedling by a Red Diamond (U.S. Plant Pat. No. 3,165) full size nectarine. I asexually reproduced the resulting plant by budding and grafting, and such reproduction of plant and fruit characteristics were true to the original plant in all respects.

DRAWING

The accompanying photograph includes different views of whole fruits, showing the characteristics of skin color and form, a characteristic fruit divided on its suture plane showing the flesh color and the stone cavity of a clingstone, and a characteristic stone.

POMOLOGICAL CHARACTERISTICS

Referring now more specifically to the pomological characteristics of this new and distinct variety of genetic dwarf nectarine tree, the following has been observed by me under the ecological conditions prevailing near Le Grand, Merced County (San Joaquin Valley), Calif., and was developed at the state of commercial ripeness in the 1983 growing season. All color plate identifications are by reference to Dictionary of Color 1950 (2nd ed) by Maerz and Paul.

TREE

General: Hardy, vigorous, very productive and regular bearing.

*Form.*—Dense, drooping, round topped.

*Size.*—Six feet tall at maturity, a large size for a genetic dwarf.

Trunk: Of medium size with shaggy, brown bark and a few medium size tan lenticles.

Branches: Of medium size with shaggy gray bark on second year and older wood and green bark on first year wood. A few small lenticles.

Leaves:

*Size.*—Length, $6\frac{1}{2}''$, width $1\frac{3}{8}''$.

*Form.*—Elliptical.

*Base.*—Acute.

*Apex.*—Acuminate.

*Margin.*—Crenate.

*Venation.*—Pinnate.

*Petiole.*—Average length, $\frac{3}{8}''$.

*Glands.*—Reniform.

*Stipules.*—Numerous, $\frac{1}{8}''$ to $\frac{1}{4}''$ long.

*Color.*—Dorsal side, dark green; ventral side, lighter green.

Flowers:

*Buds.*—Hardy, Small size, medium length, conic shape.

*Flowers.*—Blooming date: first week of March, an average date compared to other varieties.

*Size.*—Small.

*Color.*—Pink.

FRUIT

Maturity when described: About mid-picking, on August 4.

Size: Large, uniform. 3" in axial diameter, 3" in suture plant.

Form: Uniform, symmetrical. Globose except for high profile on dorsal side due to raised lips at base.

Suture: An inconspicuous line on the ventral side at base which deepens at apex; distinct suture on dorsal side commencing at base and deepening at apex to marked depression.

Surface: Ventral surface strongly rounded, dorsal surface rounded with equal lips commencing above midpoint and extending to base.

Cavity: Clingstone cavity; oval shape; numerous brown fibres.

Base: Rounded, but appearing transverse at right angle to suture line due to oblique appearance caused by lips.

Apex: Depressed ½".

Pistil point: Very small, sharp point that sometimes points in a horizontal direction rather than vertical.

Stem: Length, ¾", width 3/16".

Skin: Thin, medium tender. Tenacious to flesh. No tendency to crack. Waxy appearance.

Skin color: Resembles Chimney Red 5 L-10 blush over yellow resembling Honeysweet 11 J-6.

Flesh:

*Color.*—Resembling Ta-Ming 10 L-6 yellow, with reddish tinge at ripening.

*Texture.*—Firm, fine, extremely crisp.

*Fibres.*—Few, fine and tender. Ripens evenly.

*Flavor.*—Acid to subacid.

*Aroma.*—Slight to average.

*Eating quality.*—Excellent, the best.

STONE

Clingstone

Form: Oval.

Size: Length 1¼", width 1", breadth ¾".

Base: Gently acute.

Hilum: Narrow, oval.

*Apex.*—Rounded; flattened on right side; short, acute point.

Surface: Irregularly furrowed throughout: ventral edge only slightly pitted.

Ridges: Jagged on ventral side.

Color: Reddish when first cut, brown resembling Burnt Umber 15 A-12 when dry.

Thickness of pit wall: ¼".

Tendency to split: Slight to none.

Kernel: Ovate form, bitter taste, very viable; ½" in width, ⅝" in length.

Pellicle: Yellow with darker yellow fibres in vertical direction.

Amygdalin: Abundant.

USE

For market; fresh, long distance shipping. Keeping and shipping quality very good. Medium resistance to insects, good resistance to disease.

I claim:

1. A new and distinct variety of clingstone, genetic dwarf nectarine tree, substantially as illustrated and described, which most nearly resembles Sunbonnet (U.S. Plant Pat. No. 3,325) a genetic dwarf nectarine, but is distinguished therefrom and an improvement thereon in bearing larger fruit comparable in size to large size fruit of full size nectarine trees, which is firmer, has a redder skin color at maturity, and a waxy skin appearance.

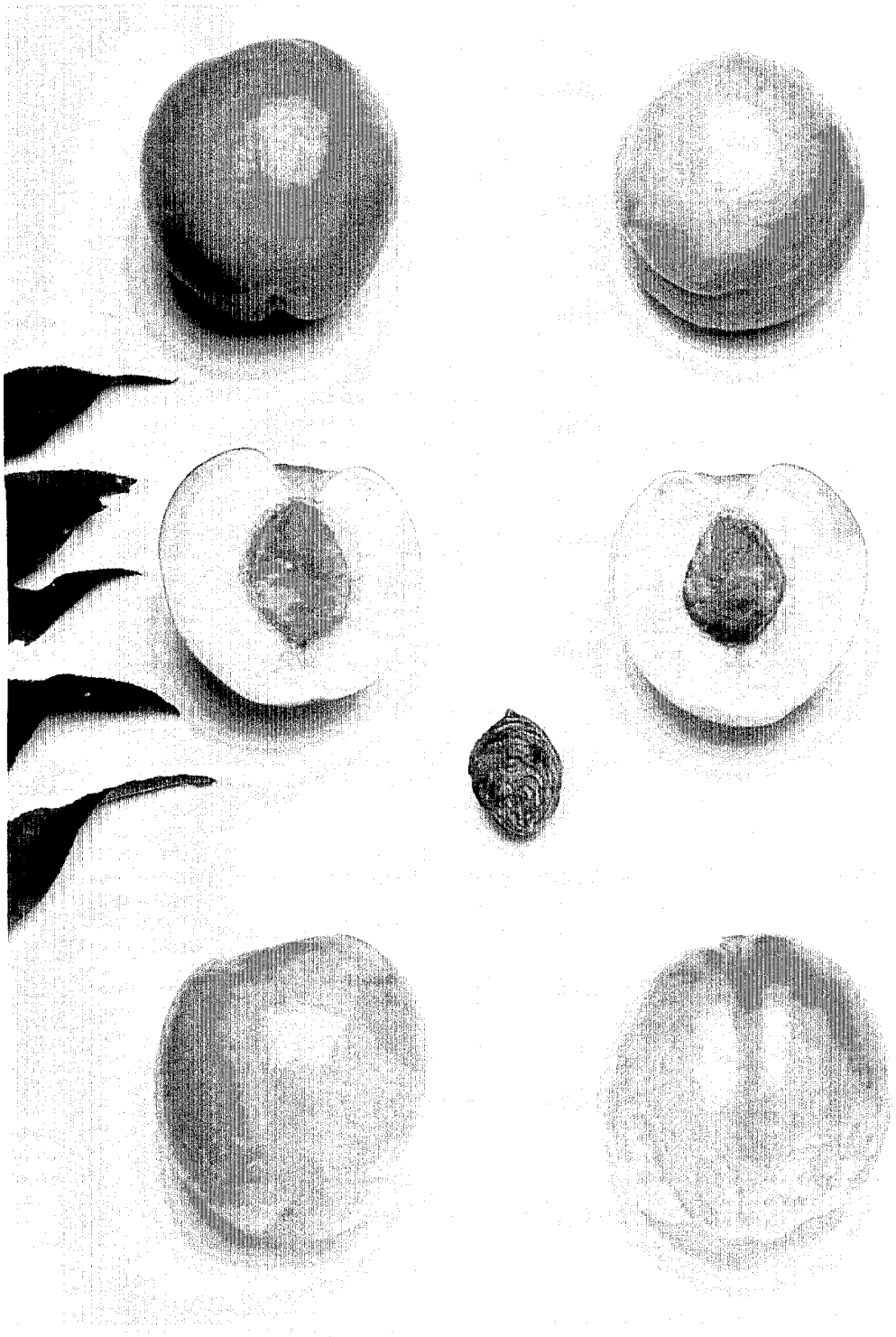

* * * * *